United States Patent [19]

Manero

[11] Patent Number: 5,478,954
[45] Date of Patent: Dec. 26, 1995

[54] PROCESS FOR PREPARING HIGHLY PURE ENANTIOMERS OF OXIRANE ALCOHOLS

[75] Inventor: Javier Manero, Frankfurt am Main, Germany

[73] Assignee: Hoechst Aktiengesellschaft, Frankfurt, Germany

[21] Appl. No.: 98,510

[22] Filed: Jul. 28, 1993

[30] Foreign Application Priority Data

Jul. 30, 1992 [DE] Germany .......................... 42 25 155.9

[51] Int. Cl.$^6$ ...................... C07D 303/14; C07D 303/02; C07F 7/08; C07B 57/00
[52] U.S. Cl. ........................... 549/541; 549/215; 549/332; 549/546; 549/555
[58] Field of Search .................................... 549/215, 538, 549/541, 555

[56] References Cited

U.S. PATENT DOCUMENTS

| | | | |
|---|---|---|---|
| 4,638,073 | 1/1987 | Walba et al. | 549/556 |
| 5,178,793 | 1/1993 | Vohra et al. | 544/335 |

FOREIGN PATENT DOCUMENTS

| | | |
|---|---|---|
| 0046033 | 2/1982 | European Pat. Off. . |
| 0454463A2 | 10/1991 | European Pat. Off. . |
| 0461285A1 | 12/1991 | European Pat. Off. . |
| 0515142A1 | 11/1992 | European Pat. Off. . |
| 2247020 | 2/1992 | United Kingdom . |

OTHER PUBLICATIONS

Perry, Chemical Engineer's Handbook, fifth edition, 1973, 17-8 through 17-13.
J. Am. Chem. Soc., "Catalytic Asymmetric Epoxidation and Kinetic Resolution: Modified Procedures Involving in Situ Derivatization", 1987, vol. 109, pp. 5765–5780.
J. Org. Chem., "Ti(O–i–Pr)—Mediated Formation of 2,3–Epithio Alcohols from 2,3–Epoxy Alcohols", 1988, vol. 53, pp. 4114–4116.

*Primary Examiner*—Rebecca Cook
*Attorney, Agent, or Firm*—Curtis, Morris & Safford

[57] ABSTRACT

Process for preparing highly pure enantiomers of oxirane alcohols, which comprises recrystallizing a mixture of the isomeric oxirane alcohols, in which the desired enantiomer is present in an excess of at least 60% ee, in a solvent or solvent mixture at a temperature just below the melting point of the oxirane alcohol.

Oxirane alcohols prepared according to the invention are distinguished by high enantiomer purity. Ferroelectric liquid crystals, which contain highly pure enantiomers of oxirane alcohols according to the invention and/or derivatives derived therefrom, have particularly short switching times.

1 Claim, No Drawings

PROCESS FOR PREPARING HIGHLY PURE ENANTIOMERS OF OXIRANE ALCOHOLS

For almost 150 years, chemists have already endeavoured to prepare chiral compounds in the form of largely pure enantiomers, either by synthesis of a single enantiomer or by resolution of the two enantiomers. A compound is chiral, if it cannot be made congruent with its mirror image. The two enantiomers of the compound are called the image and mirror image or optical antipodes. Chiral compounds are in general optically active, i.e. they rotate the plane of polarized light by a certain amount. This amount is of the same magnitude for the two enantiomers, but has different signs.

Particularly in the field of biochemistry, it is known that only one of the two enantiomers shows a certain activity, or even that the two can have completely different activities. The best known example is certainly that of the hypnotic thalidomide, of which one enantiomer acts as a hypnotic, but the other is teratogenic.

However, also in many other fields of chemistry and industry, such as plant protection and NLO, it is important to work with enantiomeric compounds which are as pure as possible. A further example of these are ferroelectric liquid crystals, i.e. those which contain chiral molecules and form tilted smectic phases.

Clark and Lagerwall have been able to show that the use of ferroelectric liquid crystal systems in very thin cells leads to optoelectric switching or indicating elements which, as compared with the conventional TN ("twisted nematic") cells, have switching times which are shorter by a factor of up to 1000 (cf. for example Lagerwall et al., "Ferroelectric Liquid Crystals for Displays", SID Symposium, October Meeting 1985, San Diego, Calif., (U.S.A.)). Based on this property and other advantageous properties, for example the possibility of bistable switching and a contrast which is almost independent of the viewing angle, FLCs are in principle very suitable for the abovementioned field of application, for example via a matrix control.

The optical switching time $\tau[\mu s]$ of ferroelectric liquid crystal systems, which is to be as short as possible, depends on the rotational viscosity of the system $\gamma[mPas]$, on the spontaneous polarization $P_s[nC/cm^2]$ and the electric field strength $E[V/m]$, according to equation:

$$\tau \sim \frac{\gamma}{P_s \times E}$$

The $P_s$ value achieved with a given chiral material is correlated with the optical purity of the material.

$P_s \approx$ optical purity

The optical purity (enantiomeric excess, ee) is defined as $$ee = \frac{A_1 - A_2}{A_1 + A_2} \times 100$$

where $A_1$ is the quantity of the enantiomer present in excess, and $A_2$ is the quantity of the optical antipode. It is therefore desirable to use exclusively a single enantiomer of a substance in ferroelectric mixtures, in order to attain the maximum possible $P_s$ value with the substances used.

Examples of substances which can be used as doping material in ferroelectrical crystal mixtures are oxirane ethers (EP 263,437) and/or oxirane esters (EP 292,954). The oxirane esters can be obtained, for example, from oxirane alcohols via the related oxirane carboxylic acids (for example Carlsen et al., J. Org. Chem., 46 (1981) 3936).

Numerous processes are known for the preparation of oxirane alcohols in the form of largely pure enantiomers. The enantioselective synthesis of oxirane alcohols from olefins has been described, for example, in EP-0,046,033 or in J. Am. Chem. Soc., 109 (1987) 5765. In spite of the good enantioselectivity and diastereoselectivity of the asymmetric epoxidation, no ee values greater than 98% (according to NMR) are reached, however.

The further "optical purification" of oxirane alcohols can in principle be carried out by reaction with a chiral auxiliary, the pair of enantiomers being converted to a pair of diastereomers, which can be separated by physical methods such as distillation, chromatography or recrystallization. Owing to the necessity of forming and subsequently decomposing derivatives, however, these processes are fundamentally much more expensive than those which work with the pure substance.

Experiments for the direct separation of the enantiomers of (2S,3S)-2,3-epoxy-1-hexanol by distillation, chromatography or normal recrystallization have been reported (see Gao et al., J. Org. Chem., 53 (1988) 4114), but no ee values greater than 98% ee have been achieved by these methods.

It is also known to obtain pure enantiomers of compounds by crystallization, by adding seed crystals of the desired enantiomer to the solution of the two enantiomers (see, for example, A. Collet, et al., Bull. Soc. Chim. 1972, 127). However, this so-called spontaneous resolution of racemates succeeds only if the racemic mixture crystallizes as a conglomerate, i.e. as a mixture of crystals of one enantiomer in each case, which is the case for only a few compounds.

It was therefore the object to provide a process, by means of which oxirane alcohols of an even higher purity of the enantiomers are obtained.

It has now been found, surprisingly, that oxirane alcohols without detectable contamination by the other diastereomers or enantiomers can be obtained by recrystallization in suitable solvents at temperatures which are just below the melting point of the oxirane alcohol, i.e. in general a few degrees below the melting point. The interval between the melting point and the temperature of the recrystallization can be the wider, the higher the melting point of the compound.

The invention therefore relates to a process for preparing highly pure enantiomers of oxirane alcohols, which comprises recrystallizing a mixture of isomeric oxirane alcohols, in which the desired enantiomer is present in an excess of at least 60% ee, in a solvent or solvent mixture at a temperature just below the melting point of the oxirane alcohol.

The invention also relates to oxirane alcohols having an optical purity greater than 99.5% ee, preferably 3-ethyloxiranemethanol, 3-propyloxiranemethanol, 3-butyloxiranemethanol and 3-pentyloxiranemethanol and especially (2S,3R)-3-propyloxiranemethanol, and to liquid crystal mixtures containing chiral compounds which were prepared from oxirane alcohols having an optical purity greater than 99% ee.

Oxirane alcohols prepared according to the invention are distinguished by high enantiomer purity. Ferroelectric liquid crystals, which contain highly pure enantiomers of oxirane alcohols according to the invention and/or derivatives derived therefrom, have particularly short switching times.

The oxirane alcohols used are preferably compounds of the formula I

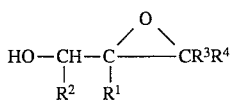

$R^1$ is hydrogen or a straight-chain or branched alkyl radical having 1 to 18 carbon atoms (with or without an asymmetric carbon atom), it also being possible for one or more —CH$_2$— groups to be replaced by —O—, —CO—, —CH=CH— or —C≡C—, cyclopropane (Δ), —Si(CH$_3$)$_2$— or 1,4-cyclohexylene, with the proviso that oxygen atoms must not be bound directly to one another, and with the proviso that at least $R^3$ or $R^4$ must be other than hydrogen if $R^1$ is not methyl, and with the proviso that neither —O—, —CO—, —CH=CH— nor —C≡C— must be bound directly to the oxirane ring, and/or one or more hydrogen atoms of the alkyl radical can be substituted by —F, —Cl, —Br, —SCN, —OCN or —N$_3$.

$R^2$ is hydrogen or a straight-chain or branched alkyl radical having 1 to 14 carbon atoms (with or without an asymmetric carbon atom), it also being possible for one or more —CH$_2$-groups to be replaced by —O—, Δ, —Si(CH$_3$)$_2$— or 1,4-cyclohexylene, with the proviso that oxygen atoms must not be bound directly to one another, and/or one or more hydrogen atoms of the alkyl radical can be substituted by —F, —Cl, —Br, —SCN, —OCN or —N$_3$.

$R^3$ and $R^4$ are hydrogen or a straight-chain or branched alkyl radical having 1 to 18 carbon atoms (with or without an asymmetric carbon atom), it also being possible for one or more —CH$_2$-groups to be replaced by —O—, —CO—, —CH=CH—, —C≡C—, Δ, —Si(CH$_3$)$_2$— or 1,4-cyclohexylene, with the proviso that oxygen atoms must not be bounded directly to one another, and with the proviso that neither —O—, —CO—, —CH=CH— nor —C≡C— must be bonded directly to the oxirane ring, and/or one or more hydrogen atoms of the alkyl radical can be substituted by —F, —Cl, —Br, —SCN, —OCN or —N$_3$.

$R^1$ and $R^3$, $R^1$ and $R^4$ as well as $R^3$ and $R^4$ together can also form a ring.

With particular preference, $R^1$ is hydrogen or a straight-chained or branched alkyl radical having 1 to 14 carbon atoms (with or without an asymmetric carbon atom), it also being possible for one or more —CH$_2$— groups to be replaced by —O—, —CH=CH—, Δ or —Si(CH$_3$)$_2$—, with the proviso that oxygen atoms must not be bound directly to one another, and with the proviso that at least $R^3$ or $R^4$ must be other than hydrogen if $R^1$ is not methyl, and with the proviso that neither —O— nor —CH=CH— must be bound directly to the oxirane ring, and/or one or more hydrogen atoms of the alkyl radical can be substituted by —F, —Cl or —Br, $R^2$ is hydrogen or a straight-chain or branched alkyl radical having 1 to 10 carbon atoms (with or without an asymmetric carbon atom), it also being possible for one or more —CH$_2$-groups to be replaced by —O— or Δ, with the proviso that oxygen atoms must not be bound directly to one another, and/or one or more hydrogen atoms of the alkyl radical can be substituted by —F or —Cl, $R^3$ and $R^4$ are hydrogen or a straight-chain or branched alkyl radical having 1 to 14 carbon atoms (with or without an asymmetric carbon atom), it also being possible for one or more —CH$_2$— groups to be replaced by —O—, —CH=CH—, Δ or —Si(CH$_3$)$_2$—, with the proviso that oxygen atoms must not be bounded directly to one another, and with the proviso that neither —O— nor —CH=CH— must be bonded directly to the oxirane ring, and/or one or more hydrogen atoms of the alkyl radical can be substituted by —F, —Cl or —Br.

$R^1$ and $R^3$, $R^1$ and $R^4$ as well as $R^3$ and $R^4$ together can also form a ring.

With very particular preference, $R^1$ is hydrogen or a straight-chained or branched alkyl radical having 1 to 12 carbon atoms (with or without an asymmetric carbon atom), it also being possible for one or more —CH$_2$— groups to be replaced by —O—, with the proviso that oxygen atoms must not be bound directly to one another, and with the proviso that at least $R^3$ or $R^4$ must be other than hydrogen if $R^1$ is not methyl, and with the proviso that —O— must not be bound directly to the oxirane ring, and/or one or more hydrogen atoms of the alkyl radical can be substituted by —F, $R^2$ is hydrogen or a straight-chain or branched alkyl radical having 1 to 6 carbon atoms (with or without an asymmetric carbon atom), it also being possible for one or more hydrogen atoms of the alkyl radical to be substituted by —F, $R^3$ and $R^4$ are hydrogen or a straight-chain or branched alkyl radical having 1 to 12 carbon atoms (with or without an asymmetric carbon atom), it also being possible for one or more —CH$_2$— groups to be replaced by —O—, Δ or —Si(CH$_3$)$_2$—, with the proviso that oxygen atoms must not be bound directly to one another, and with the proviso that —O— must not be bound directly to the oxirane ring, and/or one or more hydrogen atoms of the alkyl radical can be substituted by —F.

$R^1$ and $R^3$, $R^1$ and $R^4$ as well as $R^3$ and $R^4$ together can also form a ring.

In particular, $R^1$, $R^2$ and $R^3$ are hydrogen and $R^4$ is alkyl, and most preferably $R^4$ is ethyl, propyl, butyl or pentyl.

The (S,S), (R,R), (S,R) and (R,S) isomers of the above-mentioned compounds can in principle be obtained.

The oxirane alcohols of the formula (I) are prepared by literature methods known per se; such syntheses are described, for example, in EP 046,033 or in J. Am. Chem. Soc. 109 (1987) 5765.

By means of the process according to the invention, the oxirane alcohols indicated above can be prepared in optical purities of >99.5% ee. In order to be able to be used in the process according to the invention, the oxirane alcohols of formula (I) must contain the desired enantiomer in an excess of at least 60% ee, and preferably the desired enantiomer should be present in an excess of 70% ee, in particular of 80% ee.

The oxirane alcohol to be purified is dissolved in a suitable organic solvent, preferably at elevated temperatures, in particular at the boiling point of the solvent. The solvents used are preferably aliphatic and aromatic hydrocarbons, such as pentane, hexane, heptane, cyclohexane, methylcyclohexane, benzene, toluene and xylenes, halogenated aliphatic and aromatic hydrocarbons such as dichloromethane, chloroform, carbon tetrachloride, 1,2-dichloroethane and chlorobenzene, cyclic and acyclic ethers such as diethyl ether, dibutyl ether, tetrahydrofuran and 1,4-dioxane, and also esters such as ethyl acetate or amides such as dimethylformamide. It is particularly preferred to use alkanes, in particular n-alkanes. Mixtures of the solvents mentioned can also be used. The concentration of oxirane alcohol in the solution is between 0.1 gram per liter of solution up to the saturation concentration at the boiling point of the solvent. Concentrations between 1 gram of oxirane alcohol per liter of solvent and the saturation concentration of the oxirane alcohol at the boiling point of the solvent are preferred, and concentrations between 20 grams of oxirane alcohol per liter of solvent and the saturation concentration of the oxirane alcohol at the boiling point of the solvent are particularly preferred. Concentrations between 50 grams of oxirane alcohol per liter of solvent and 500 grams of oxirane alcohol per liter of solvent, or the saturation concentration at the boiling point of the solvent, if this is lower, are very particularly preferred.

After the oxirane alcohol has been dissolved, a filtration is carried out if necessary, in order to separate off undissolved impurities.

Subsequently, the solution is kept for a certain period, preferably 48 hours, in particular 18 hours, at a temperature just below the melting point of the oxirane alcohol, i.e. in general few degrees below the melting point. Temperatures of up to 20° C. below the melting point of the oxirane alcohol are preferred, temperatures of 0.01 to 15.0 degrees below the melting point are particularly preferred, and 0.05 to 10.0 degrees below the melting point are very particularly preferred, and 0.1 to 5.0 degrees below the melting point are especially preferred.

After some time, the desired enantiomer crystallizes out in the pure form. It is isolated, for example, by filtration with suction, if appropriate with cooling.

The determination of the optical purity, i.e. of the ee value, can be carried out by various methods with which those skilled in the art are familiar. In principle, a mixture of enantiomers can be examined by chiral or achiral methods. In the chiral methods, diastereomeric interactions are observed and, in the achiral methods, the mixture of enantiomers is converted by reaction with a chiral auxiliary into diastereomeric compounds which can be analyzed on the basis of their different physical and chemical properties.

Suitable chiral auxiliaries are, depending on the functionalization of the mixture of enantiomers, various pure enantiomers of natural substances (alcohols, amines, amino acids, acids, etc.) and specially developed compounds, for example Mosher's acid: α methoxy-α-trifluoromethyl-α-phenylacetic acid. The quantitative analysis of the diastereomers can be carried out, for example, by NMR spectroscopy, GC or HPLC.

Suitable chiral methods are, for example a) the measurement of the value of rotation, in which case, however, the wavelength-dependent value of rotation of the pure enantiomer must be known and significantly different from zero, and the mixture of enantiomers must be available in sufficient quantities and analytical purity;

b) the NMR-spectroscopic measurement of the mixture of enantiomers in a chiral or chirally doped medium, such as can be carried out, for example, with chiral Europium complexes such as $Eu(tfc)_3$, $Eu(hfc)_3$, or c) gas chromatography on chiral columns, for example on cyclodextrins, as described, inter alia, by V. Schurig, D. Wistuba, Angew. Chem. 98 (1986) 1008, and W. A. König et al., Angew. Chem. 101 (1989) 180. This method is in principle very suitable because of its high precision and sensitivity (ee values greater than 99% can be determined to four significant digits). In this method, it can be advantageous to convert the mixture of enantiomers to be examined into suitable volatile and/or chemically or physically stable derivatives, such as silyl compounds, acetyl compounds or trifluoromethyl compounds.

The highly pure enantiomers of oxirane alcohols, prepared according to the invention, can be used in all fields in which compounds of this type are of interest, such as in the pharmaceutical chemistry, in the chemistry of plant protection agents or in the field of non-linear optics. The use as starting material for substances, which are suitable as doping materials for ferroelectric liquid crystal mixtures, for example oxirane ethers and oxirane esters, is preferred.

The invention is explained in more detail by the Examples:

EXAMPLE 1

Synthesis of (2S,3R)-propyloxiranemethanol 19.56 g of powdered molecular sieve (3 Å), 1.5 l of dichloromethane, 17.9 ml (60 mmol) of titanium isopropylate and 12.36 ml (36.01 mmol) of L(+)-diethyl tartrate are first introduced at 0° C. under $N_2$ into a 4-necked 4 l flask. 200 ml (1 mol) of t-butyl hydroperoxide (5M in heptane) are added dropwise in the course of 20 minutes at −20° C. with stirring to the suspension. Stirring is continued for 20 minutes at −20° C. and a solution of 50 g (500 mmol) of cis-2-hexen-1-ol in 50 ml of dichloromethane is then added dropwise. Subsequently, the mixture is held for 20 hours at −5° to −10° C. At 0° C., a solution of 165.3 g (60.13 mmol) of $FeSO_4.7H_2O$ and 50.08 g (300.4 mmol) of L(+)-tartaric acid in 770 ml of $H_2O$ is added, the phases are separated and the aqueous phase is extracted with 3×250 ml of diethyl ether. The combined organic phases are dried over $MgSO_4$, filtered with suction through a glass frit and concentrated in a rotary evaporator. The residue is taken up in 1.3 l of diethyl ether, a solution of 24.6 g of NaOH in 350 ml of saturated aqueous NaCl solution is added with fast stirring at 0°–4° C. in the course of 15 minutes, and stirring is continued for 1 hour at 0° to 3° C. 500 ml of $H_2O$ are added, the phases are separated and the aqueous phase is extracted with 5×250 ml of diethyl ether. The combined organic phases are dried over $MgSO_4$, filtered with suction through a glass frit, and the solvent is stripped off in a rotary evaporator. The oil thus obtained is dried for 45 minutes in an oil pump vacuum. Crude yield: 56.13 g. According to column chromatography (silica gel, 2/1 heptane/ethyl acetate), this gives 46.7 g of (2S,3R)-3-propyloxiranemethanol of an optical purity of 81.1% ee (GC). Melting point: −6° C.

EXAMPLE 2

10 Grams of (2S,3R)-3-propyloxiranemethanol from Example 1 are dissolved in 100 ml of hexane and held for 12 hours at −8° C. White crystals precipitate, which are filtered off with suction at the said temperature.

EXAMPLE 3

100 mg of (2S,3R)-3-propyloxiranemethanol from Example 2 are filled with 400 mg of N-methyl-bis-(trifluoroacetyl)amide (MBTFA) and 1 ml of dichloromethane into a pressure-resistant 2 ml phial and encapsulated. After heating for 30 minutes at 100° C. 1 μl of the derivative solution is injected into a gas chromatograph (Dani 8500, made by Dani).

| Column: | 50 m fused silica capillary column of 0.25 mm internal diameter. | |
|---|---|---|
| Stationary phase: | 0.25 μm permethylated β-cyclodextrin (® Lipodex β-PM, made by Macherey + Nagel) | |
| GC conditions: | carrier gas: helium at 1.5 bar upstream pressure = 3 ml/minute | |
| | injector: | split injection at 250° C. |
| | detector: | 100 ml/minute |
| | oven: | 100°C. |

In contrast to materials from Example 1 and from the Comparison Example, the material from Example 2, recrystallized according to the invention, gives only a single signal. Thus, pure enantiomers of compounds are obtained by the process according to the invention.

Comparison Example 10 g of (2S,3R)-3-propyloxiranemethanol obtained according to Example 1 are dissolved in 100 ml of hexane and recrystallized at −30° C. With respect to chiral purity, the product obtained is identical to the starting material employed.

I claim:

1. A process for preparing an enantiomer of an oxirane alcohol, which comprises recrystallizing a mixture comprising the two enantiomers of said oxirane alcohol, in which the desired enantiomer is present in an excess of at least 60% enantiomeric excess (ee), in an organic solvent or organic solvent mixture selected from the group consisting of aliphatic and aromatic hydrocarbons, halogenated aliphatic and aromatic hydrocarbons, ethers, esters and amides at a temperature of 0.1 to 5 degrees Celsius below the melting point of said oxirane alcohol, wherein the oxirane alcohol is a compound of formula (I),

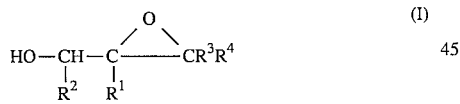

where $R^1$ is hydrogen or a straight-chain or branched alkyl radical having 1 to 18 carbon atoms with or without an asymmetric carbon atom, in which one or more —$CH_2$— groups optionally are replaced by —O—, —CO—, —CH=CH—, —C≡C—, cyclopropane (Δ), —Si($CH_3$)$_2$— or 1,4-cyclohexylene, with the proviso that oxygen atoms must not be bound directly to one another, and with the proviso that at least $R^3$ or $R^4$ must be other than hydrogen if $R^1$ is not methyl, and with the proviso that neither —O—, —CO—, —CH=CH— nor —C≡C— must be bound directly to the oxirane ring; and in which one or more hydrogen atoms of the alkyl radical optionally are substituted by —F, —Cl, —Br, —SCN, —OCN or —$N_3$;

$R^2$ is hydrogen or a straight-chain or branched alkyl radical having 1 to 14 carbon atoms (with or without an asymmetric carbon atom), in which one or more —$CH_2$— groups optionally are replaced by —O—, cyclopropane (Δ), —Si($CH_3$)$_2$— or 1,4-cyclohexylene, with the proviso that oxygen atoms must not be bound directly to one another, and in which one or more hydrogen atoms of the alkyl radical optionally are substituted by —F, —Cl, —SCN, —OCN or —$N_3$, $R^3$ and $R^4$ are hydrogen or a straight-chain or branched alkyl radical having 1 to 18 carbon atoms (with or without an asymmetric carbon atom), in which one or more —$CH_2$— groups optionally are replaced by —O—, —CO—, cyclopropane (Δ), —CH=CH—, —C≡C—, —Si($CH_3$)$_2$— or 1,4-cyclohexylene, with the proviso that oxygen atoms must not be bound directly to one another, and with the proviso that neither —O—, —CO—, —CH=CH— nor —C≡C— must be bound directly to the oxirane ring, and in which one or more hydrogen atoms of the alkyl radical optionally are substituted by —F, —Cl, —Br, —SCN, —OCN or —$N_3$, and in which $R^1$ and $R^3$, $R^1$ and $R^4$ or $R^3$ and $R^4$ together optionally form a ring, at a concentration between 0.1 g/l of solution up to the saturation concentration at the boiling point of the solvent.

* * * * *